US00PP30896P2

(12) United States Plant Patent
Smith

(10) Patent No.: US PP30,896 P2
(45) Date of Patent: Sep. 24, 2019

(54) ***CHRYSANTHEMUM* PLANT NAMED 'CIFZ0064'**

(50) Latin Name: ***Chrysanthemum* x *morifolium***
Varietal Denomination: CIFZ0064

(71) Applicant: SYNGENTA PARTICIPATIONS AG, Basel (CH)

(72) Inventor: Mark A. Smith, Alva, FL (US)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/932,537

(22) Filed: Mar. 13, 2018

(51) Int. Cl.
*A01H 5/02* (2018.01)
*A01H 6/14* (2018.01)

(52) U.S. Cl.
USPC ..... Plt./286

(58) Field of Classification Search
USPC ..... Plt./286
See application file for complete search history.

*Primary Examiner* — Susan McCormick Ewoldt
(74) *Attorney, Agent, or Firm* — Dale Skalla

(57) ABSTRACT

A new garden type *Chrysanthemum* plant named 'CIFZ0064' particularly distinguished by the medium size plant with upright to outwardly spreading and uniform mounded plant habit, a medium flower size with dark pink/purple flower color and a natural season response in late September/early October.

1 Drawing Sheet

Figure 1:
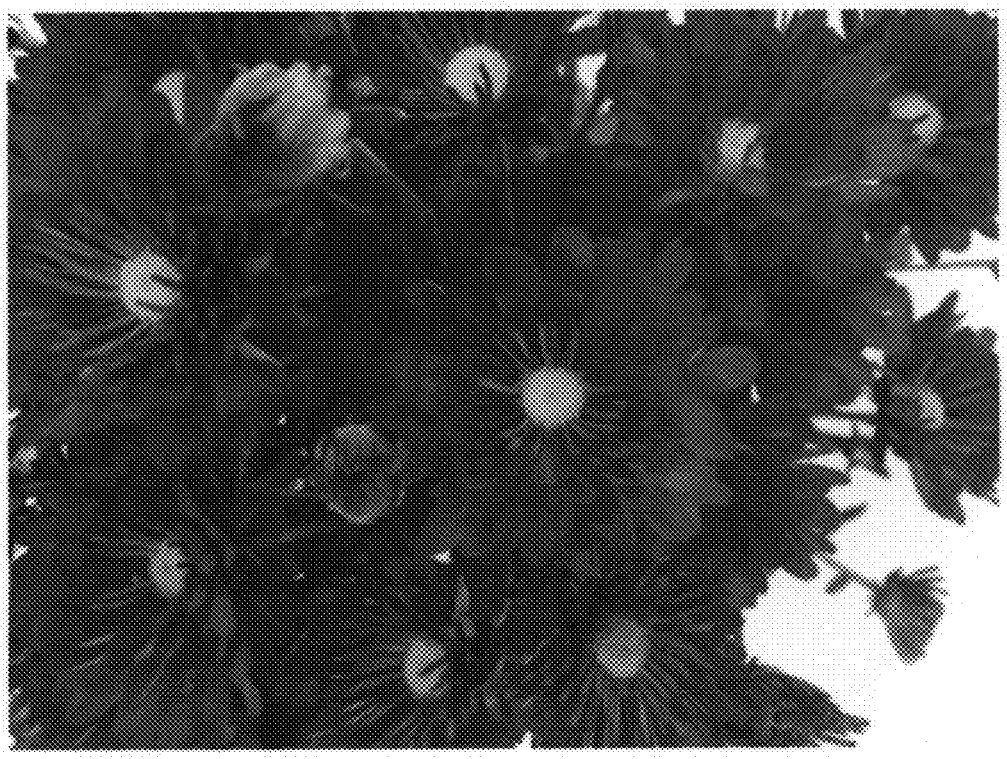

Latin name of the genus and species of the plant claimed: *Chrysanthemum* x *morifolium.*
Varietal denomination: 'CIFZ0064'.

BACKGROUND OF THE NEW PLANT

The present invention comprises a new *Chrysanthemum*, botanically known as *Chrysanthemum* x *morifolium*, and hereinafter referred to by the variety name 'CIFZ0064'.

'CIFZ0064' is a product of a planned breeding program. The new cultivar has medium size plant with upright to outwardly spreading and uniform mounded plant habit, a medium flower size with dark pink/purple flower color, and a natural season response in late September/early October 'CIFZ0064' originated from a cross made in November 2007 in Tenjo, Columbia. Seeds were sown in June, 2013 in Gilroy, Calif. and 'CIFZ0064' was selected from the resulting population on October 21 in Monroeville, N.J.

The female parent was the variety 'Velours rouge' (not patented). When compared to the female parent, 'CIFZ0064' has:

1) Larger flower size with more disc florets and dark pink while female parent has light red flower color
2) Blackcloth response is similar but natural season response is three weeks faster than the female parent
3) More uniform flowering than female parent
4) Similar plant habit but larger overall size than female parent The male parent was the variety 'Alisha Dark Pink' ('Yoalisha', U.S. Plant Pat. No. 18,995). When compared to the male parent, 'CIFZ0064' has:

1) Similar plant habit but larger overall size than male parent
2) More vigor compared to male parent
3) Less likely to split compared to male parent The first act of asexual reproduction of 'CIFZ0064' was accomplished when vegetative cuttings were propagated from the initial selection in January 2014 in Mebane, N.C.

BRIEF SUMMARY OF INVENTION

Horticultural examination of plants grown from cuttings of the plant initiated in January 2014 and continuing thereafter, has demonstrated that the combination of characteristics as herein disclosed for 'CIFZ0064' are firmly fixed and are retained through successive generations of asexual reproduction.

'CIFZ0064' has not been observed under all possible environmental conditions. The phenotype may vary significantly with variations in environment such as temperature, light intensity and day length.

A Plant Breeder's Right for this cultivar has not been applied for. 'CIFZ0064' has not been made publicly available prior to the effective filing date of this application, notwithstanding any disclosure that may have been made less than one year prior to the effective filing date of this application by the inventor or another who obtained 'CIFZ0064' directly from the inventor.

The following traits have been repeatedly observed and are determined to be basic characteristics of the new variety. The combination of these characteristics distinguishes this *Chrysanthemum* as a new and distinct variety.

BRIEF DESCRIPTION OF THE PHOTOGRAPHS

The accompanying photographic drawing shows typical flower and foliage characteristics of 'CIFZ0064' with colors being as true as possible with an illustration of this type.

Figure 2:
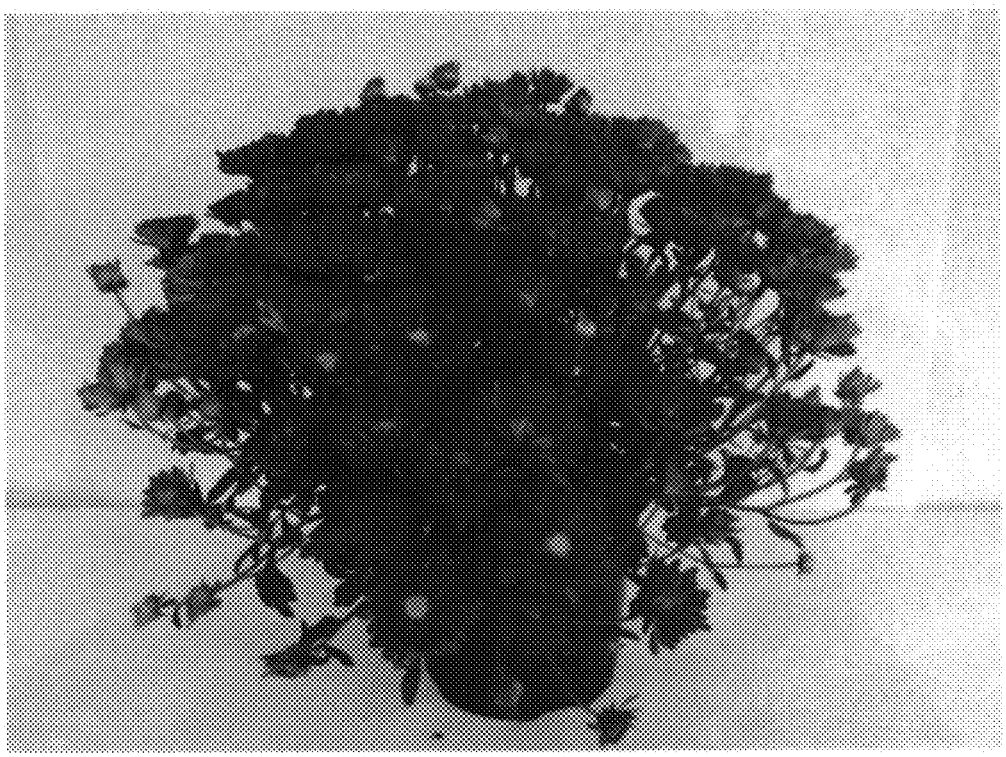

The photographic drawings show in FIG. 1 a close view of flower of the new variety and in FIG. 2 a flowering plant from an outdoor trial.

The aforementioned photographs: FIG. 1 and FIG. 2 were taken in August 2017 both showing a plant from the same blackcloth indoor trial in Gilroy, Calif. These plants were about 10 weeks of age. One rooted cutting per pot had been planted in a one gallon pot, not pinched in week 24, and black clothed from week 25. Plants started flowering in August.

DETAILED BOTANICAL DESCRIPTION

The measurements were taken in Gilroy, Calif., in August 2017 on the plants from the aforementioned trial.

Color references are made to The Royal Horticultural Society Colour Chart (R.H.S.) 2001.

TABLE 1

DIFFERENCES BETWEEN THE NEW VARIETY 'CIFZ0064' AND TWO MOST SIMILAR VARIETIES:

| | 'CIFL0064' | 'Stacy' (U.S. Plant Pat. No. 11,852) |
|---|---|---|
| Flowering response (blackcloth): | Similar to a bit slower | Similar to a bit faster |
| Flowering response (natural): | 5 days slower | 5 days faster |
| Flower color: | Dark pink/lavender colour, no Two tone colour | Two-tone color, lighter pink/ lavender color |
| Flower size: | Smaller | Bigger |
| Plants, stems, flexibility: | Flexible plant | Less flexible, may break when compressed |
| Plant habit or size: | Larger overall size with similar plant habit, but less clubby than Stacy | Smaller plant but more clubby than 'CIFZ0064' |

TABLE 2

| | 'CIFZ0064' | 'Amphion' (U.S. Pat. No. 13,271) |
|---|---|---|
| Flowering response (blackcloth): | Similar | Similar |
| Flowering response (natural): | Similar | Similar |
| Colour fading: | Less fading | More fading |
| Flower color: | Darker lavender/ pink color | Lighter lavender/ pink color |
| Flower longevity: | Longer lasting | Shorter lasting |
| Flower size: | Large | Smaller |
| Plant habit or size: | Similar | Similar |

Plant:

*Form, growth and habit.*—Herbaceous garden-type, stems upright and outwardly spreading, freely branching, strong and moderately vigorous growth habit.

*Plant height* (*above soil*).—12-15 cm.

*Plant height* (*inflorescence included*).—17-20 cm.

*Plant width.*—34-37 cm.

Roots:

*Number of days to initiate roots.*—About 4 days at about 22° C.

*Number of days to produce a rooted cutting.*—14-16 days at 22° C.

*Type.*—Fine, fibrous, free branching.

*Color.*—RHS N155B but whiter.

Foliage:

*Arrangement.*—Alternate.

*Immature leaf, color upper surface.*—RHS 137A.

*Immature leaf, color lower surface.*—RHS 137D.

*Mature leaf, color, upper surface.*—Between RHS 137A and 137B.

*Mature leaf, color lower surface.*—Closest to RHS 137D.

*Length.*—4.0-4.5 cm.

*Width.*—3.4-3.6 cm.

*Shape.*—Ovate, with distinct lobes.

*Base shape.*—Attenuate.

*Apex shape.*—Mucronate.

*Margin.*—5-lobed (palmate), edge dentate.

*Texture, upper surface.*—Bifid hairs.

*Texture, lower surface.*—Bifid hairs.

*Color of veins, upper surface.*—RHS 138B.

*Color of veins, lower surface.*—RHS N138B.

*Pattern of veining.*—Palmate.

*Petiole color.*—RHS 138A.

*Petiole length.*—1.7-1.9 cm.

*Diameter.*—0.15-0.2 cm.

*Texture.*—Covered with bifid hairs.

Stem:

*Quantity of main branches per plant.*—5-7.

*Color of stem.*—RHS 138A to 138B.

*Length of stem.*—12-15 cm.

*Diameter.*—0.4-0.5 cm.

*Length of internodes.*—0.3-1.2 cm.

*Texture.*—Bifid hairs.

*Color of peduncle.*—RHS 138A.

*Length of peduncle.*—5.5-6.0 cm.

*Peduncle diameter.*—0.2 cm.

*Texture.*—Bifid hairs.

Inflorescence:

*Type.*—Compositae, solitary, semi-double type inflorescences borne terminally above foliage, ray and disc florets arranged on a capitulum.

*Quantity of short days to flowering* (*response time*).—Approximately 6 weeks.

*Natural season flowering.*—Early to mid-October.

*Quantity of inflorescences per plant.*—80-100.

*Lastingness of individual blooms on the plant.*—About six weeks from first color.

*Fragrance.*—Slightly spicy.

Bud (when showing color):

*Color.*—Closest to RHS N77B, overlain with RHS N155A.

*Length.*—1.0 cm.

*Width.*—1.1 cm.

*Shape.*—Oblate.

Immature inflorescence:

*Diameter.*—2.0-2.4 cm.

*Color of ray florets, upper surface.*—RHS 61A.

*Color of ray florets, lower surface.*—RHS 61A, overlain with RHS 155A.

Mature inflorescence:

*Diameter.*—4.6-5.1 cm.

*Depth.*—1.6-2.1 cm.

*Total diameter of disc.*—0.7-0.9 cm.

*Receptacle color.*—RHS 144C.

*Receptacle height.*—0.2 cm.

*Receptacle diameter.*—0.4-0.5 cm.

Ray florets:

*Average quantity of florets.*—Between 200 and 220 in several whorls.

*Color of florets, upper surface* (*abaxial*).—Between RHS 70A and RHS 70B.

*Color inner surface* (*adaxial*).—RHS 70A overlain with RHS 155A.

*Length.*—1.6-1.9 cm.

*Width/diameter.*—0.4-0.5 cm.

*Shape.*—Elliptical.

*Apex shape.*—Most obtuse and dentate.

*Base shape.*—Tube.

*Margin.*—Entire, small incisions may occur at the tip.

*Texture, upper surface*.—Papillate.
*Lower surface*.—Papillate.
Dish florets: 100-120.
*Width*.—0.1 cm.
*Length*.—0.4 cm.
*Color*.—RHS 6A at apex, RHS N144D at base.
Phyllaries:
*Quantity*.—20-25.
*Color, upper surface*.—RHS 138B.
*Color, lower surface*.—RHS 138A.
*Length*.—1.0-1.3 cm.
*Width*.—0.2-0.3 cm.
*Shape*.—Lanceolate.
*Apex shape*.—Acute.
*Base*.—Fused.
*Margins*.—Entire.
*Texture, upper surface*.—Glabrous.
*Texture, lower surface*.—Canescent.
Reproductive organs:
*Pistil*.—One.
*Length*.—0.3-0.5 cm.
*Style color*.—RHS 150A.
*Style length*.—0.2-0.3 cm.
*Stigma color*.—RHS 7C.
*Stigma shape*.—Bi-parted.
*Ovary color*.—RHS 145C.
*Ovary length*.—0.15 cm.
*Ovary width*.—0.1 cm.
Androecium:
*Stamens*.—1, found on only disc florets.
*Color of filaments*.—RHS 2C.
*Length filaments*.—0.2 cm.
*Anther color*.—RHS 13B.
*Anther length*.—0.2 cm.
*Anther shape*.—Oval to club shaped.
*Color of pollen*.—RHS 13B.
*Pollen amount*.—Moderate.
*Fertility*.—Has pollen so it can be fertile as a male.
*Disease/pest resistance*.—Has not been determined to date.

What is claimed is:

1. A new and distinct variety of *Chrysanthemum* plant named 'CIFZ0064' substantially as illustrated and described herein.

* * * * *